United States Patent [19]

Evans et al.

[11] 4,174,349
[45] Nov. 13, 1979

[54] PREPARATION OF FLUOROORGANIC COMPOUNDS WITH CALCIUM FLUORIDE

[75] Inventors: Francis E. Evans, Hamburg, N.Y.; Morris B. Berenbaum, Summit, N.J.; Richard E. Eibeck, Orchard Park; Martin A. Robinson, East Amherst, both of N.Y.

[73] Assignee: Allied Chemical Corporation, Morris Township, Morris County, N.J.

[21] Appl. No.: 955,679

[22] Filed: Oct. 30, 1978

[51] Int. Cl.² ............ C07C 17/10; C07C 17/12; C07C 17/14; C07C 51/58
[52] U.S. Cl. .............. 260/544 F; 260/96 HA; 260/586 R; 260/590 R; 260/591; 260/592; 260/593 H; 260/598; 260/599; 260/601 H; 260/646; 260/648 F; 260/649 F; 260/650 F; 260/653.8; 260/694; 568/655; 568/656; 568/669; 568/683; 568/684
[58] Field of Search ............ 260/544 F, 648 F, 646, 260/649 F, 650 F, 653.8, 586 R, 590 R, 591, 592, 593 H, 598, 599, 601 H, 694, 96 HA; 568/655, 656, 669, 683, 684

[56] References Cited

U.S. PATENT DOCUMENTS

| 2,614,129 | 10/1952 | McBee et al. | 260/544 F |
|---|---|---|---|
| 2,696,503 | 12/1954 | Prichard | 260/544 F |
| 2,859,245 | 11/1958 | Smith | 260/544 F |
| 3,632,643 | 1/1972 | Prichard | 260/544 F |
| 3,696,150 | 10/1972 | Lidstein et al. | 568/683 |
| 3,991,108 | 11/1976 | Jordan | 260/544 F |

FOREIGN PATENT DOCUMENTS

| 710843 | 6/1965 | Canada | 260/544 F |
|---|---|---|---|
| 2117650 | 10/1972 | Fed. Rep. of Germany | 260/544 F |
| 2442883 | 3/1976 | Fed. Rep. of Germany | 260/544 F |

OTHER PUBLICATIONS

Simons et al., "JACS" vol. 65, 2064–2065 (1943).
Stephens et al., "Quart. Rev", vol. 162, pp. 44–51 (1962).
Sheppard, "J. Org. Chem.," vol. 29, No. 1, pp. 1–11 (1964).
Weygand, "Prep. Org. Chem.", pp. 204–209 (1972), John Wiley & Sons.

Primary Examiner—Norman Morgenstern
Attorney, Agent, or Firm—Jay P. Friedenson

[57] ABSTRACT

Fluoroorganic compounds are prepared by reacting a haloorganic starting material in which at least one halo atom is replaceable with a fluorine atom by metathetical exchange, with calcium fluoride in the presence of a crown ether and an anhydrous, polar, basic organic solvent which complexes with the calcium ion and contains no —OH groups, at a temperature and for a period of time adequate to effect fluorination.

25 Claims, No Drawings

PREPARATION OF FLUOROORGANIC COMPOUNDS WITH CALCIUM FLUORIDE

BACKGROUND OF THE INVENTION

The conventional preparation of fluoroorganic compounds involves the reaction of chloro-, bromo-, or iodoorganic compounds with ionic fluorides such as KF. Prior workers found that when crown ethers are used to chelate the potassium ion in such ionic fluorides, the fluoride reactivity is enhanced and yields of the corresponding organic fluorides are significantly increased.

KF is prepared from HF and HF is derived from fluorspar (calcium fluoride, $CaF_2$). If $CaF_2$ could be used directly as the fluoride source in such fluorination reactions, then the cost of preparing the fluoroorganic compounds could be reduced significantly. Unfortunately, $CaF_2$ exists as a stable crystal with a high crystal lattice energy and is generally considered to be inert under most conditions other than that of high acidity and high temperature (above 300° C.)

We considered the possibility that $CaF_2$ might also be activated by crown ethers; however, our initial attempts to conduct fluorination reactions with $CaF_2$ in the presence of crown ethers failed.

It is accordingly an object of this invention to provide a means of activating $CaF_2$ sufficiently to serve as a fluorinating agent for the general preparation of fluoroorganic compounds from haloorganic starting materials in which at least one halo atom is replaceable with a fluorine atom by metathetical exchange.

Other objects and advantages of the invention will become apparent from the following description.

SUMMARY OF THE INVENTION

We have found that $CaF_2$ can be activated sufficiently to enable it to fluorinate haloorganic starting materials in which at least one halo atom is replaceable with a fluorine atom by metathetical exchange, by carrying out the reaction with $CaF_2$ in the presence of a cage compound and an anhydrous, polar, basic organic solvent which contains no —OH groups and which solubilizes the cage compound, the starting material and the $CaF_2$, at a temperature and for a period of time adequate to effect fluorination. The choice of solvent is critical, for the use of cage compounds alone will not sufficiently activate the $CaF_2$ and the presence of other diverse solvents will similarly not influence the activation significantly. Conversely, the presence of solvents including the ones described herein, in the absence of cage compounds, has insufficient influence on the activation of the $CaF_2$ for fluorination purposes. It is the critical combination of the presence of a cage compound together with the presence of a critically defined solvent which activates the $CaF_2$ sufficiently to accomplish the objects of the invention.

DETAILED DESCRIPTION OF THE INVENTION

Any haloorganic compound in which at least one halo atom is replaceable with a fluorine atom by metathetical exchange is suitable for use as a starting material in accordance with the present invention. It is apparent that such starting material must contain at least one halo atom which is selected from the group consisting of chlorine, bromine and iodine. Candidate compounds for metathetical exchange (i.e. replacement with no valence change) are easily recognizable by those skilled in the art. Such starting materials can be aliphatic or aromatic, polycyclic or heterocyclic and may contain a multiplicity of halo atoms including fluorine and diverse hetero atoms such as O, N and S and moieties such as $NO_2$, $SO_3^-$ and $SO_2$. The carbon content of such starting materials is not critical. Compounds containing from one up to several hundred carbon atoms or even substantially more would be suitable.

Preferred classes of haloorganic starting materials suitable for use in accordance with the invention process are selected from the group consisting of alkyl halides, acyl halides, haloacyl halides, haloethers, haloketones, haloaldehydes, aryl halides and aralkyl halides in which the halide is selected from chloride, bromide and iodide. The preferred halide is chloride. Exemplary starting materials include perchloroethylene, trichloroethylene, chloroform, bromodecane, acetyl chloride, benzoyl chloride, trifluoroacetyl chloride, trichloroacetyl chloride, bischloromethyl ether, hexachlorodimethyl ether, hexachloroacetone, trichloroacetaldehyde, 2,4-dinitrochlorobenzene, 2,4-dichloronitrobenzene, benzyl chloride, benzyl bromide, polyvinyl chloride, chlorinated polyethylene, chlorinated polypropylene, polychloroprene and polyvinylidene chloride.

Naturally occurring $CaF_2$ (fluorspar) and synthetically prepared $CaF_2$ are suitable for use in accordance with the invention process. Since $CaF_2$ is a solid, the reaction is dependent on the rate of dissolution or reaction at the solid-liquid interface. Accordingly, as a rule, the smaller the solid particle or the greater the surface area of the particle, the more easily it will participate in the reaction. Accordingly, the calcium fluoride employed should preferably be finely divided—at least 10 mesh (by Tyler Screen designation in ASTM E11) and, still preferably, be at least 100 mesh.

By "cage compounds" are meant both crown ethers and their macro-polycyclic counterparts known as "crypts." Crown ethers are a well known class of compounds, the preparation and identity of which are fully described in U.S. Pat. No. 3,687,978. Crown ethers are macro-monocyclic polyethers and may be generally defined as being rings containing repeating ($-X-CH_2-CH_2-)_n$ units. For the cases wherein $X=O$, the repeating unit is ethyleneoxy. If the carbon portion is one carbon shorter the repeating unit would be methyleneoxy. If longer carbon chains are involved, the CH—CH interactions will exert an effect on the overall conformation of the macroring.

The generic name "crown" is suggested by the similarity of the molecular models to a regal crown and by the abilities of these compounds to "crown" cations by complexation. The smallest value of n which fits the above definition is 1,4-dioxane. No smaller molecule satisfies the "repeating" requirement of the definition. The crown compound designated 18-crown-6 is 1,4,7,10,13,16-hexaoxacyclooctadecane. 18 represents the total number of atoms in the ring, crown is the class name and 6 is the total number of hetero atoms in the ring portion of the macrocycle. The principal variation in X according to the above formula is to substitute NH or NR for O. S, P and $CH_2$ have also been substituted for O. These are only representative examples of the many varieties possible. For a more comprehensive description of crown ether structures, reference is made to the above-mentioned U.S. Pat. No. 3,687,978 which also gives a detailed description of how to synthesize such molecules. Also see J. J. Christensen et al., Chem. Rev., 74, 351 (1974); J. S. Bradshaw et al. Heterocycl. Chem. 11, 649 (1974) and C. J. Pedersen, et al., Angew. Chem., Int. Ed. Engl., 11, 16 (1972). Exemplary crown compounds are 1,4,7,10,13,16-hexaoxacyclooctadecane (18-crown-6); dibenzo-18-crown-6; 15-crown-5; monobenzo-15-crown-5; dicyclohexyl-18-crown-6; monocyclohexyl-15-crown-5; dibenzo-24-crown-8 and dicyclohexyl-24-crown-8.

The crypt compounds are likewise a well-known class of compounds generally being the essentially three-dimensioned macrocyclic counterparts of the crown compounds. The crypt compounds can be generally characterized as bicyclic diamine polyethers in which the ether linkages may be substituted and in which additional groups may be present or substituted as discussed for the crown ethers. A description of crypt compounds may be found in PCR Incorp.'s Technical Bulletin entitled "KRYPTOFIX" (Polyoxadiazamacrobicyclic Compounds) and also in J. Org. Chem., Vol. 42, No. 10, 1977, 2A.

Exemplary crypt compounds are 4,7,13,16,21,24-hexaoxa-1,10-diazabicyclo[8.8.8]-hexacosane (crypt 222); 4,7,13,16,21-pentaoxa-1,10-diazabicyclo[8.8.5]-tricosane (crypt 221); 4,7,13,18-tetraoxa-1,10-diazabicyclo[8.5.5]-eicosane (crypt 211); 1,7,10,16-tetraoxa-4,13-diazacyclooctadecane (diaza-18-crown-6) and 5,6-benzo-4,7,13,16,21,24-hexaoxa-1,10-diazabicyclo[8.8.8]-hexacosane (benzo crypt 222).

The preferred cage compounds are 18-crown-6, crypt 222 and crypt 221.

The solvent may be any anhydrous, polar, basic organic solvent which contains no —OH groups and which solubilizes the cage compound, starting material and $CaF_2$.

The term "polar" is used in the usual sense understood by the art to connote an assemblage of atoms or subatomic particles having equal electric charges of opposite sign separated by a finite distance (*The Condensed Chemical Dictionary*, 9th Ed., p.318).

Similarly, the term "basic" is used in its ordinary sense to connote either a Lowry-Bronsted base which is any molecular or ionic substance that can combine with a proton (hydrogen ion) to form a new compound, or a Lewis base which is defined as any substance that provides a pair of electrons for a covalent bond with a Lewis acid (*The Condensed Chemical Dictionary*, 9th Ed. p. 93).

By "solubilizes" is meant bringing all three components into contact by dissolving, complexing, suspending or otherwise. Illustrative of bases which meet the subject definition are dimethyl formamide, formamide, triethylamine, dimethylacetamide, diethylacetamide, dissubstituted aromatic amine and suitably substituted heterocyclic amines. Others will readily occur to those of ordinary skill in the art. A preferred group of solvents are those containing a basic nitrogen with no hydrogen bonded thereto, such as dimethylformamide, dimethylacetamide, triethylamine and trimethylamine.

There is no criticality for the molar ratio of $CaF_2$ to the haloorganic starting material in the process of the invention. Obviously, a sufficient amount of $CaF_2$ fluorinating agent should be employed to optimize yields. Large excesses will not deleteriously affect the reaction. Generally, from about 0.1–10:1 molar ratio of $CaF_2$ to haloorganic starting material should be employed but preferably, from about 1–3:1 molar ratio of $CaF_2$ to haloorganic starting material should be employed.

The amount of cage compound is not critical and may range over a wide latitude. Generally, the higher the concentration the greater the acceleration of the exchange reaction; however, the amount of cage compound employed should be practicably balanced by cost. In actual practice the minimum amount required to effect a reasonable rate of reaction should be employed and this will vary depending upon the identity of the haloorganic starting material, the solvent, as well as the other reaction parameters chosen, such as temperature. The optimum amount of crown ether to use in a given system may be readily determined by those skilled in the art. Levels as low as 0.0005 mole per mole of haloorganic starting material were found to be catalytic. Generally, molar ratios of the cage compounds to the haloorganic starting materials which should be employed lie between about 0.0005–10:1 and preferably between about 0.01–1:1 and, still preferably, between about 0.01–1:1.

Temperatures are not critical except in combination with the other reaction parameters discussed herein. Temperature does have an influence on the rate of reaction and elevated temperatures may be required in a particular environment to initiate the fluorination reaction and/or to maximize yield. Generally, temperatures employed lie between ambient temperature up to the boiling point of the solvent with temperatures of at least 70° C. being preferred. Higher temperatures may be advantageously employed at super-atmospheric pressures. Preferred temperature ranges generally lie between about 70°–130° C. and, even more preferably, between about 75°–125° C. Operative and optimum temperatures for a given system will depend upon the haloorganic starting material employed, choice of the crown ether and the solvent and may be readily ascertained by those skilled in the art.

Reaction time is also not critical except in combination with the other parameters discussed herein. Reaction time does have an influence on yields insofar as assurance that the reaction goes to completion. Here again, the preferred times will vary depending upon the particular system involved. Generally, reaction times vary from about 1–120 hours with reaction times of at least 2 hours being preferred. Preferred reaction times lie between about 2–24 hours. The optimum contact time for a given system may be readily ascertained by those skilled in the art.

EXAMPLES 1–11

In the following examples all analyses were carried out by gas chromatography.

The general procedure used for all of the examples was as follows with any changes noted in the Table.

A 250 ml. 3-necked flask was equipped with a condenser, agitator, thermometer and nitrogen purge. The exit from the condenser was connected to a cold trap held at −50° to −80° C. After purging the flask with dry nitrogen to ensure a dry atmosphere, the following reagents were charged in the order shown:

Haloorganic starting material—0.1 mole
Solvent—50 grams
Calcium fluoride (precipitated, powdered calcium fluoride, passing 200 mesh)—0.11 mole
Cage compound—0.0038 mole The reaction mixture was then heated to 70°–75° C. and held for 18 hours under a slight nitrogen purge. The contents of the cold trap were analyzed. The yield of fluorinated product, if any, was estimated based on the relative amounts of unreacted starting material found. The results are shown in the following Table:

TABLE

| Example | Solvent | Haloorganic starting material | Cage Compound | Fluoroorganic Product (wt %) |
|---|---|---|---|---|
| 1 | acetic acid | acetyl chloride | 18-crown-6 | none |
| 2 | acetonitrile | acetyl chloride | 18-crown-6 | acetyl fluoride 5-10% |
| 3 | dimethyl formamide | acetyl chloride | " | acetyl fluoride (greater than 50%)* |
| 4 | dimethyl formamide | acetyl chloride | 15-crown-5** | acetyl fluoride 5% |
| 5 | dimethyl formamide | acetyl chloride | dibenzo 18-crown-6*** | acetyl fluoride 10-15% |
| 6 | dimethyl formamide | acetyl chloride | crypt 222 (.0019 mole) | acetyl fluoride 60-65% |
| 7 | dimethyl formamide | 1-bromodecane | 18-crown-6 (.0076 mole) | 1-fluorodecane (Between 1 & 5%)**** |
| 8 | dimethyl acetamide | acetyl chloride | 18-crown-6 | acetyl fluoride 60-65% |
| 9 | triethylamine | acetyl chloride | " | acetyl fluoride 10-20% |
| 10 | formamide | acetyl chloride | " | acetyl fluoride 5-10% |
| 11 | dimethyl formamide | acetyl chloride | dibenzo-18-crown-6 | acetyl chloride (10-15% after 14-18 hours) |

*Repetition of this experiment with careful drying of all equipment and prolonged purging with nitrogen increased the yield to over 80%, an indication that the sensitivity of acetyl fluoride to hydrolysilanes a significant factor.
**1,4,7,10,13 pentaoxacyclopentadexane
***dibenzo-1,4,7,10,13,16 hexaoxacyclooctadecane-2,11-diene
****This reaction was conducted at 100°-110° C. over a period of 17 hours.

Examples 1 and 2 demonstrate that without use of the critically defined solvents of the invention, CaF$_2$ is not sufficiently activated to fluorinate the starting material.

In the absence of the cage compound, basic solvents such as formamide, do not promote the reactivity of CaF$_2$ under similar conditions.

Although negative fluorination results have been obtained even by using crown ethers and the critically defined solvents in accordance with the invention, positive results can be achieved by increasing the temperature and/or reaction times suitably for a particular environment.

We claim:

1. The method which comprises reacting a haloorganic starting material in which at least one halo atom is replaceable with a fluorine atom by metathetical exchange, with calcium fluoride in the presence of a cage compound and an anhydrous polar, basic organic solvent which contains no —OH groups and which solubilizes the cage compound, starting material and calcium fluoride, at a temperature and for a period of time adequate to effect fluorination.

2. The method according to claim 1 in which the haloorganic starting material is selected from the group consisting of alkyl halides, acyl halides, haloacyl halides, haloethers, haloketones, haloaldehydes, aryl halides and aralkyl halides.

3. The method according to claim 1 in which the haloorganic starting material is an alkyl chloride.

4. The method according to claim 1 in which the haloorganic starting material is an acyl chloride.

5. The method according to claim 1 in which the haloorganic starting material is a haloacyl chloride.

6. The method according to claim 1 in which the haloorganic starting material is a chloroether.

7. The method according to claim 1 in which the haloorganic starting material is a chloroketone.

8. The method according to claim 1 in which the haloorganic starting material is a chloroaldehyde.

9. The method according to claim 1 in which the haloorganic starting material is an aryl chloride.

10. The method according to claim 1 in which the haloorganic starting material is an arylalkyl chloride.

11. The method according to claim 1 in which the cage compound is a crypt compound.

12. The method according to claim 1 in which the cage compound is a crown compound.

13. The method according to claim 12 in which the crown compound is 1,4,7,10,13,16-hexaoxacyclooctadecane.

14. The method according to claim 11 in which the crypt compound is 4,7,13,16,21,24-hexaoxa-1,10-diazabicyclo[8.8.8.]-hexacosane.

15. The method according to claim 16 in which the solvent is formamide.

16. The method according to claim 1 in which the solvent contains a basic nitrogen with no hydrogen attached thereto.

17. The method according to claim 16 in which the solvent is dimethylformamide.

18. The method according to claim 16 in which the solvent is dimethylacetamide.

19. The method according to claim 16 in which the solvent is triethylamine.

20. The method according to claim 16 in which the solvent is trimethylamine.

21. The method according to claim 16 in which the solvent is dimethylacetamide.

22. The method according to claim 1 which is carried out at about 70°–130° C. for at least two hours.

23. The method according to claim 1 wherein the solvent is dimethyl formamide and the cage compound is 1,4,7,10,13,16-hexaoxacyclooctadecane.

24. The method according to claim 1 wherein the solvent is dimethyl formamide and the cage compound is 4,7,13,15,21,24-hexaoxa-1,10-diazabicyclo[8.8.8]-hexacosane.

25. The method according to claim 1 wherein the solvent is dimethyl formamide and the cage compound is 4,7,13,16,21-pentaoxa-1,10-diazabicyclo[8.8.5]-tricosane.

* * * * *